United States Patent [19]

Huber et al.

[11] Patent Number: 4,957,011

[45] Date of Patent: * Sep. 18, 1990

[54] WEATHERING TESTING SYSTEM

[75] Inventors: James V. Huber, Oak Park; Kurt P. Scott, Chicago; Rudolph J. Leber, Palatine, all of Ill.

[73] Assignee: Atlas Electric Devices Co., Chicago, Ill.

[*] Notice: The portion of the term of this patent subsequent to Jul. 4, 2006 has been disclaimed.

[21] Appl. No.: 345,658

[22] Filed: May 1, 1989

Related U.S. Application Data

[63] Continuation of Ser. No. 131,221, Dec. 10, 1987, Pat. No. 4,843,893.

[51] Int. Cl.$^5$ .............................................. G01N 25/00
[52] U.S. Cl. ...................................... 73/865.6; 374/5; 374/138; 374/57; 236/DIG. 9
[58] Field of Search ...................... 73/159, 150, 865.6; 374/57, 138, 5, 7; 236/DIG. 9, 49.3

[56] References Cited

U.S. PATENT DOCUMENTS

| | | | |
|---|---|---|---|
| 3,224,266 | 12/1965 | Klippert | 73/150 R |
| 3,488,681 | 1/1970 | Mita et al. | 73/159 X |
| 3,886,791 | 6/1975 | Grossman | 73/865.6 X |
| 3,983,742 | 10/1976 | Suga | 73/865.6 X |
| 4,627,287 | 12/1986 | Suga . | |
| 4,704,903 | 11/1987 | Suga et al. . | |
| 4,807,247 | 2/1989 | Robbins | 73/865.6 X |

OTHER PUBLICATIONS

Atlas Bulletin No. 1282 (Jun. 1983).
Atlas Bulletin No. 1360 (Oct. 1986).
"Atlas Sun Spots", vol. 16, Issue 37 (Autumn 1986).

*Primary Examiner*—Daniel M. Yasich
*Attorney, Agent, or Firm*—Gerstman & Ellis, Ltd.

[57] ABSTRACT

A testing system for determining accelerated weathering characteristics of various items such as fabrics and paint samples. Rack means are provided for carrying samples to be tested. A source of irradiation of the inner-facing surfaces of the samples carried on the rack is also provided, along with a blower system for directing a stream of air through the rack. In accordance with this invention, a generally conical member is positioned in the stream of air to redirect the stream outwardly in a generally conical flow path. The generally conical flow path is positioned by the conical member to flow across the inner-facing surfaces of the samples carried on the rack.

13 Claims, 1 Drawing Sheet

WEATHERING TESTING SYSTEM

This is a continuation of application Ser. No. 131,221, filed Dec. 10, 1987, now U.S. Pat. No. 4,843,893.

BACKGROUND OF THE INVENTION

Systems for testing the weathering and lightfastness of products such as fabric samples, painted panels, and plastics are presently available, being sold for example by the Atlas Electric Devices Company of Chicago, Ill. These devices test the weathering and lightfastness properties of materials and products under closely controlled conditions.

In the natural environment, light, heat, and moisture combine synergistically to cause optical, mechanical, and chemical changes in products which are exposed to outdoor weathering conditions. Typically, the apparatus can be used to obtain such weathering data on an accelerated time basis, to permit product manufacturers to gain information as to how their products will stand up to weathering over the months or years.

Suga, U.S. Pat. No. 4,627,287 discloses a light resistant tester for testing the lightfastness and weathering capabilities of products, where air is circulated through the system to control the temperature of samples being tested so that they are not overheated by the radiation source, which typically may be a xenon lamp. The patent is directed to a technique for air cooling the system without creating nonuniform cooling of the samples being tested.

In accordance with this invention, an improvement to weathering testing systems is provided in which samples being tested may be uniformly air cooled with greater efficiency, requiring the circulation of less air. This enables the use of a lower powered air pump which operates at a lower speed of operation, for savings of power, while lengthening the useful life of the air pump, which can thus be a lower capacity, lower cost pump. Additionally, the weathering testing system of this invention may have the sample temperature controlled in an automated manner so that the temperatures of the samples may be reliably maintained at a predetermined value without constant monitoring.

DESCRIPTION OF THE INVENTION

In this invention, a weathering testing system is provided which comprises rack means for carrying samples to be tested, means for irradiating the inner-facing surfaces of said samples carried on the rack, and blower means for directing a stream of air through the rack.

In accordance with this invention, a generally conical member is positioned in the stream of air to redirect the stream of air outwardly in a generally conical flow path. The generally conical flow path is positioned by the geometry and position of the conical member to flow across the inner-facing surfaces of the samples carried on the rack means. This is in contrast to the teaching of the previously cited patent, in which efforts are made to prevent the direct flow of the main stream of air across the samples. Instead, some of the flow in the cited patent is directed towards the light source in the center of the system, and most of the remainder of the flow is directed to the outside of the frame and sample holders, for primary cooling of the sample holders through their outer surfaces rather than their inner surfaces as in this invention.

Accordingly, by this invention, the majority of the stream of air generated by the blower means passes directly across the inner-facing surfaces of the samples carried on the rack means. It has been found that, under this circumstance, good uniformity of cooling can be provided to all samples present. At the same time, as stated above, a lower capacity air blower can be used, for significant cost savings both in cost of manufacture and operation.

Preferably, temperature sensing means, typically of electronic nature, are carried on the rack in the stream of air in electrical connection with automatic (preferably electronic) control means for the blower means. As the result of this, the output of the blower means may be adjusted in a manner responsive to temperatures sensed, to maintain a predetermined temperature at the sensing means. The temperature sensing means may be positioned at a distance from the light source that corresponds to the positioning and distances of the various samples being tested, so that the temperature sensed is the temperature at which the samples are being exposed.

The rack means and irradiating means described above are typically carried in a housing. Conduit means may be provided for recirculating air from the housing back to the blower means, for incorporation into the stream of air by the blower. Additionally, means may be provided (such as a power humidifier) for inserting moisture droplets into a stream of air, for use when high humidity test conditions are desired Additionally, heating means may be provided to warm the supply of water which feeds the humidifier.

The rack means preferably holds the samples to be tested in substantially equidistant relation with the center of the irradiating means, so that the irradiation and heating conditions of the respective samples in the apparatus are substantially constant.

In the system of this invention, it is the faces of the samples for testing that are being directly cooled by an air stream. This provides greater control and uniformity of cooling than is possible where most of the air stream impinges against the back of the test samples. In that instance, the cooling must take place by conduction through the thickness of the test sample, rather than mostly by direct exchange of heat from the faces of the test samples to the rapidly moving air stream. Also, the use of this system makes possible a desired disposition of samples for testing in a roughly spherical array about the light source, as shown in the drawings herein. With such a disposition of the test samples, it would not be feasible to cool the test samples which are most remote from the air stream in uniform manner with the other samples in that circumstance where the air stream blows against the outer surfaces of the test samples. Such flow along the outer surfaces of the most remote samples would almost certainly be inhibited by its positioning so that flow stagnation would develop, and the more remote test samples would be heated to a higher degree than the other samples.

DESCRIPTION OF SPECIFIC EMBODIMENT

Figure 1:
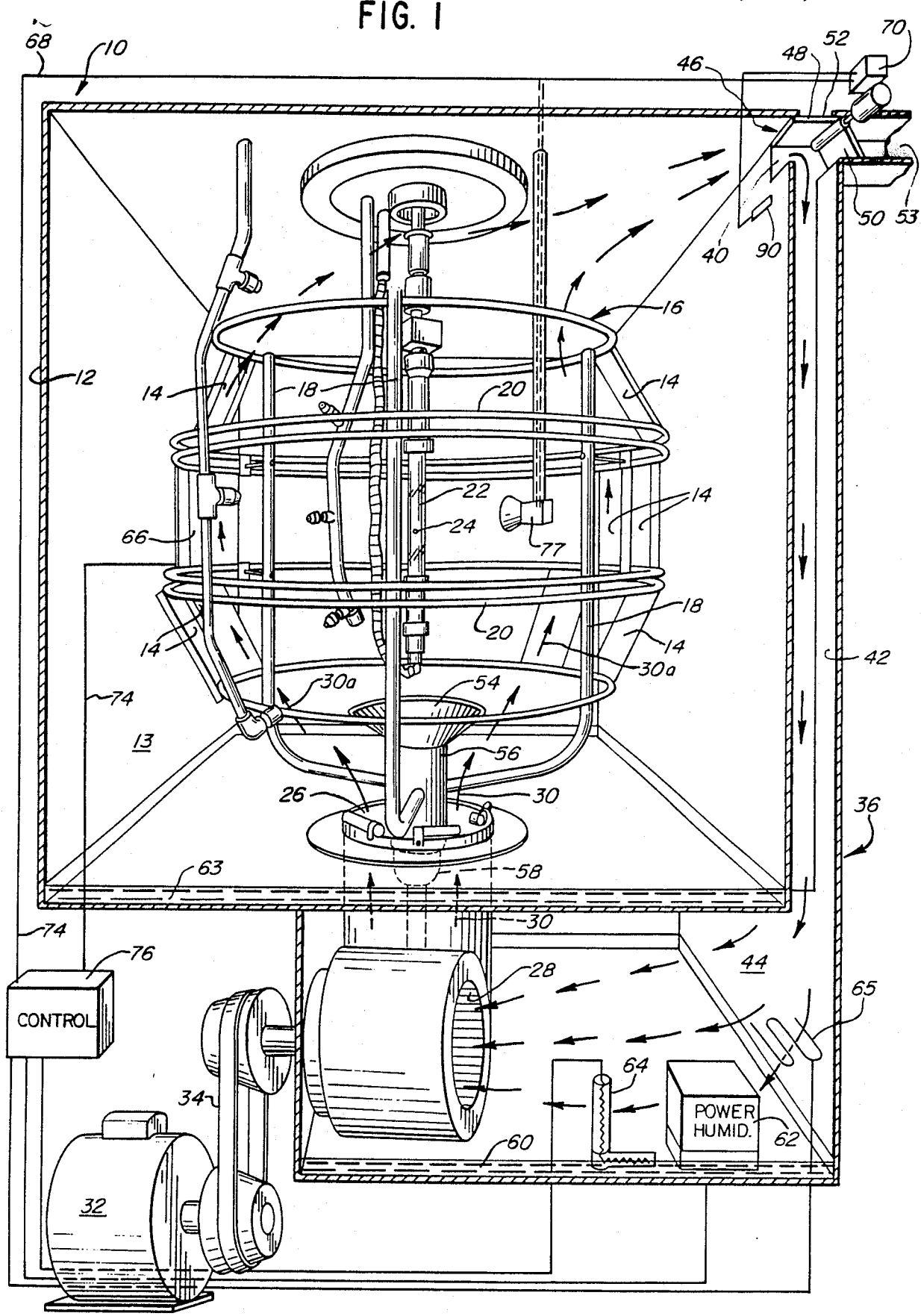
FIG. 1 is an elevational view of the weathering testing system of this invention, with portions of the housing broken away and shown in partially schematic form.

Referring to the drawing, the weathering testing system 10 of this invention includes a first housing 12 which defines a central holding chamber 13. Test samples 14 may be pieces of fabric held in a holder member, painted panels, pieces of plastic, or the like, for which weathering resistance data is desired.

Test samples 14 may be carried on a rack 16, which may be made as shown out of a roughly cylindrical array of stainless steel struts 18, to which test samples 14 may be attached. A series of central rings 20 may project outwardly from the remainder of rack 16, to permit test samples 14 to be attached to rack 16 in a roughly spherical array, as mentioned above. At the center of the spherical array of test panels 14, is the light source, which specifically may be a xenon lamp 22 of a conventionally available type. The rack 16 is positioned so that the attached samples 14 are all substantially equidistant from the center 24 of xenon lamp 22 so that all samples 14 receive substantially uniform irradiation, being all positioned substantially perpendicular to radii extending outwardly from center 24 of lamp 22 to each test sample 14.

The bottom of housing 12 defines an aperture 26 A conventional centrifugal air blower 28 is provided to blow a stream of air 30 upwardly through aperture 26, to be directed through rack 16. Air blower 28 may be conventionally operated by electric motor 32, connected to blower 28 through belt drive system 34.

Blower 28 occupies a second chamber which is defined by second housing portion 36. Circulating air is drawn from the top of the chamber 13 defined by first housing through aperture 40, to be normally recirculated through conduit 42 back to chamber 44 defined by second housing portion 36, to feed blower 28.

Pivoting damper or valve member 46 defines a pair of pivotable flaps 48, 50. In the position of valve 46 shown, recirculation takes place. However, valve member 46 may be rotated about 45 degrees counterclockwise to open aperture 52 to provide a flow exit vent for the system, and also to open air inlet port 53. Thus, the unit is converted into a nonrecirculating system.

In accordance with this invention, generally conical member 54, which may be either of the shape of a hollow funnel, or a solid shape, is attached by sleeve 56 to a stationary support member 58, which may be conventionally carried on the wall of second housing portion 36.

Accordingly, as blower 28 directs air stream 30 upwardly through aperture 26, the air stream is deflected by conical member 54 outwardly in a generally conical flow path 30a, which is positioned to flow across the inner-facing surfaces of samples 14, i.e. those surfaces which face xenon lamp 22. Thus it can be seen that a direct stream of air of conical air stream 30a flows across each of the inner-facing surfaces of samples 14. It turns out that this flow can provide good temperature uniformity among the respective samples 14, even when the flow rate of air stream 30 is significantly reduced from the corresponding flow rates of similarly sized test systems of the prior art.

Additionally, second housing 36 may contain an amount of water 60 in its bottom area, which feeds powered humidifier 62. Humidifier 62 may be of a conventional design to emit a fog of water droplets, which are incorporated into the flowing air and particularly air stream 30, for testing as desired of test samples under high radiation and high humidity conditions. Housing 12 can define a trough 63 to receive water that settles out of the air stream.

Heater 64 may heat water 60 to provide added overall heat to the system as the heated water circulates in the form of droplets, so that the variables of radiation, humidity present, and temperature may be independently controlled in the apparatus of this invention. Refrigeration coil and system 65 may provide cooling to the air flow when desired.

Additionally, a temperature sensor such as black panel sensor 66 may be carried on rack 16 in a position corresponding to the positions of samples for testing 14. Black panel sensor 66 may be of convention design, and may be connected by electrical conductors 68 a 74 to control member 70, which may be conventionally designed to operate damper 46 between its rotary positions, to either cause recirculation of air flow in the position shown, or by counterclockwise rotation (for example 45 degrees) cause air to be expelled through aperture 52 and to be drawn into conduit 42 through aperture 53.

Accordingly, the system is warmed, particularly by xenon light 22, while in the recirculation mode, but the system may be cooled by opening damper 46 to any desired degree so that less recirculation takes place, and warmed by closing damper 46 to increase recirculation. Thus, by temperature data provided by black panel 66, control unit 70 can operate damper 46 to control the temperature sensed by test samples 14. Additionally, control unit 70, through control unit 76, can control heater 64 and refrigeration coil 65 for further flexibility of temperature control of the air stream.

Thus both black panel and dry bulb temperatures can be controlled. The dry bulb temperature may be sensed by sensor 90 in the air stream and may be connected to control member 70. Hence, by temperature data provided by dry bulb sensor 90, control unit 70 can control the air stream temperature. Additionally, black panel 66 may be connected to control unit 76 which can control the rate of operation of motor 32 for air blower 28 as a means of controlling black panel temperature. Accordingly, both black panel and dry bulb temperatures can be controlled. This improves correlation on many temperature sensitive materials. Control unit 76 may also control humidifier 62, heater 64, and refrigeration system 65.

Light sensing rod 77 is provided to monitor the intensity of light emitted by lamp 22.

Thus, a weathering testing system is provided in accordance with this invention in which significant uniformity of cooling is provided to the test samples, as well as uniformity of radiation to which they are exposed. The system may be provided for automatic temperature control, and provides efficiencies both of initial cost and operation due to the new, efficient air flow pattern provided therein.

The above has been offered for illustrative purposes only and is not intended to limit the scope of this application, which is as defined in the claims below.

That which is claimed is:

1. In a weathering testing system which comprises rack means for carrying samples to be tested, means for irradiating the inner-facing surfaces of said samples carried on said rack, and blower means for directing a stream of air through said rack, the improvement comprising, in combination: said system carrying temperature sensing means comprising a first temperature sensor positioned to be irradiated by said irradiating means and a second temperature sensor positioned to be less influenced by radiation from said irradiating means than said first temperature sensor, said temperature sensors being positioned in said stream of air, said first temperature sensor being in electrical connection with first automatic control means for the air flow, said first automatic control means being operably connected to said blower means, whereby the output of said blower means, is selectively adjusted responsive to the temperature sensed at said first sensor, the second temperature sensor being in electrical connection with second automatic control means for regulating a fresh air supply.

2. The system of claim 1 in which said rack means and irradiating means are carried in a housing, and conduit means are provided for recirculating air from said housing back to said blower means for incorporation into said stream of air, venting aperture means being provided in said housing plus damper means controlling flow through said aperture means, whereby air may be either recirculated or passed in a single pass through said system depending on the position of said damper means, said second automatic control means providing control of the damper means responsive to said second temperature sensor whereby the temperature in the system is independently controlled by varying the output of said blower means and varying the position of said damper means.

3. The system of claim 2 in which said sensor is carried on said rack at a position spaced from the irradiating means by a distance corresponding to the positions of the samples to be tested, and said second temperature sensor is positioned more remotely from said irradiating means than said first sensor, whereby said automatic control means functions in response to temperature readings from both said first and said second sensors.

4. The system of claim 3 in which said first temperature sensor is a black panel sensor.

5. The system of claim 1 in which means are provided for inserting water droplets into said stream of air.

6. The system of claim 1 in which said rack means holds said samples in an approximately spherical array about said light source.

7. The system of claim 1 in which means are provided for heating and cooling said stream of air.

8. The system of claim 1 in which said first temperature sensor is a black panel sensor.

9. In a weathering testing system which comprises rack means for carrying samples to be tested, means for irradiating inner-facing surfaces of said samples carried on said rack means, and blower means for directing a stream of air through said rack means, the improvement comprising, in combination: said system carrying black panel temperature sensing means positioned in said stream of air and exposed to said irradiating means; said temperature sensing means being in electrical connection with automatic control means for the air flow, said automatic control means being operably connected to said blower means, whereby the output of said blower means may be adjusted responsive to the temperature sensed at said sensing means, said rack means and irradiating means being carried in a housing; conduit means provided for recirculating air from said housing back to said blower means for incorporation into said stream of air; venting aperture means being provided in the housing plus damper means controlling flow through said aperture means, whereby air may be either recirculated or passed in a single pass through said system depending on the position of said damper means; a second temperature sensor positioned more remotely from said irradiating means than said black panel sensing means; and automatic control means providing control of the damper means responsive to said temperature sensor, whereby the temperature in the system can be independently controlled by varying the output of said blower means and varying the position of said damper means.

10. The system of claim 9 in which said black panel temperature sensing means is carried on said rack means at a position spaced from the irradiating means by a distance corresponding to the positions of the samples to be tested.

11. The system of claim 10 in which said rack means holds said samples in an approximately spherical array about said light source.

12. The system of claim 11 in which means are provided for heating and cooling said stream of air.

13. The system of claim 12 in which means are provided for inserting water droplets into said stream of air.

* * * * *